United States Patent
O'Lenick et al.

(10) Patent No.: US 8,277,787 B1
(45) Date of Patent: *Oct. 2, 2012

(54) ALKOXYLATED GUERBET CITRATE POLYESTERS

(75) Inventors: Kevin A. O'Lenick, Dacula, GA (US); Andrew J. O'Lenick, Dacula, GA (US); Anthony J. O'Lenick, Jr., Dacula, GA (US)

(73) Assignee: SurfaTech Corporation, Lawrenceville, GA (US)

( * ) Notice: Subject to any disclaimer, the term of this patent is extended or adjusted under 35 U.S.C. 154(b) by 287 days.

This patent is subject to a terminal disclaimer.

(21) Appl. No.: 12/586,710

(22) Filed: Sep. 28, 2009

Related U.S. Application Data

(60) Provisional application No. 61/271,259, filed on Jul. 20, 2009.

(51) Int. Cl.
*A61K 8/02* (2006.01)
*A61K 8/85* (2006.01)
*C08G 63/06* (2006.01)
*C08G 63/12* (2006.01)

(52) U.S. Cl. ............... 424/70.11; 424/401; 528/425; 528/271

(58) Field of Classification Search .................. None
See application file for complete search history.

(56) References Cited

U.S. PATENT DOCUMENTS 4,868,236 A * 9/1989 O'Lenick, Jr. ............... 524/308
5,089,658 A   2/1992 Elmore et al.

* cited by examiner

*Primary Examiner* — Richard Schnizer
*Assistant Examiner* — Alma Pipic

(57) ABSTRACT

The present invention has as its objective a series of citrate polyesters that have based upon guerbet alcohols reacted with citric acid, and crosslinked by water soluble diols, resulting in polymers with improved water solubility. These polymers have a very low viscosity when one considers the molecular weight, and are ideally suited to personal care applications due to their unique feel delivered from aqueous solution or emulsions.

2 Claims, No Drawings

ALKOXYLATED GUERBET CITRATE POLYESTERS

RELATED APPLICATIONS

This application claims priority to and benefit of U.S. Provisional Application No. 61/271,259 filed Jul. 20, 2009, the disclosure of which is incorporated herein for all purposes.

FIELD OF THE INVENTION

The present invention is directed to a series of polymeric citrate esters that have unique improved compatibility with water, are themselves liquid, and have an outstanding feel when applied to the skin from aqueous formulations.

BACKGROUND OF THE INVENTION

Citric acid is a common material of natural origin. The structure is:

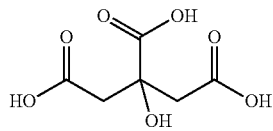

CAS Registry Number: 77-92-9
CA Index Name: 1,2,3-Propanetricarboxylic acid, 2-hydroxy- Citric acid is made by fermentation; using cultures of *Aspergillus niger* are fed on a sucrose or glucose-containing medium.

Citric acid is one of a series of compounds involved in the physiological oxidation of fats, proteins, and carbohydrates to carbon dioxide and water. This series of chemical reactions is central to nearly all metabolic reactions, and is the source of two-thirds of the food-derived energy in higher organisms. Krebs received the 1953 Nobel Prize in Physiology or Medicine for the discovery. The series of reactions is known by various names, including the citric acid cycle, the Krebs cycle, and the tricarboxylic acid cycle Citrate esters are known. They conform to the following structure:

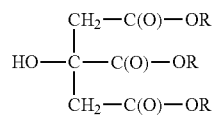

The esters are made by the reaction of fatty alcohols with citric acid.

U.S. Pat. No. 4,292,192 issued to Hooper, et al. teaches that Detergent bars for personal washing are given a deodorant property by including an ester of citric acid. The ester may be an acetyl derivative. The amount of ester used will be in the range of from about 0.3% to about 3%. Examples of the esters are triethyl citrate and acetyl tributyl citrate.

U.S. Pat. No. 2,122,716 describes long chain esters of citric acid, e.g., tridodecyl citrate, which have been used as plasticizers for resinous compositions.

U.S. Pat. Nos. 3,239,555 and 3,241,992 disclose bis-citric acid esters made by esterifying the acid groups with C1 to C18 alcohols and coupling the esters with dibasic acids. Such esters are useful as plasticizers for plastics.

U.S. Pat. No. 3,251,792, the acid groups of citric acid are esterified with alkyl, aryl, cycloalkyl and haloaryl alcohols and the hydroxyl group is esterified with a carbonyl compound. Such compounds are used as stabilizers for polypropylene.

U.S. Pat. No. 5,089,658 issued Feb. 18, 1992 to Elmore et al, is directed to citric acid esters. In one aspect, this invention pertains to citric acid esters, which contain at least one primary or secondary hydroxyl group. In another aspect, this invention relates to citric acid esters, which are reactive diluents. In still another aspect, this invention pertains to citric esters, which are pigment dispersants. The citric ester compositions of this invention are useful as reactive diluents for high solids thermosetting coating composition and as pigment dispersants for use in thermosetting coatings U.S. Pat. No. 4,868,236 to O'Lenick discloses a guerbet citric ester and polymers thereof useful in plastic lubrication.

None of these patents provide polyester derivatives of mixed fatty esters of citrate as envisioned by the present invention.

THE INVENTION

Objective of the Invention

The present invention has as its objective a series of citrate polyesters that have based upon guerbet alcohols reacted with citric acid, and crosslinked by water soluble diols, selected from the group polyoxyethylene, polyoxyalkylene and combinations thereof. These polymers have a very low viscosity when one considers the molecular weight, and are ideally suited to personal care applications due to their unique feel, when delivered from aqueous solution.

The present invention also has an objective a process for treating hair and skin with the guerbet citrate polyesters.

Other objectives will become clear as one reads the specification and claims herein.

SUMMARY OF THE INVENTION

The present invention discloses a polyester made by the reaction of a mixture of guerbet alcohols reacted with citric acid and a water soluble diol crosslinker.

DETAILED DESCRIPTION OF THE INVENTION

The present invention relates to a polyester that conforms to the following structure:

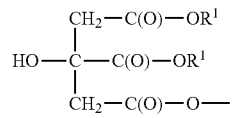 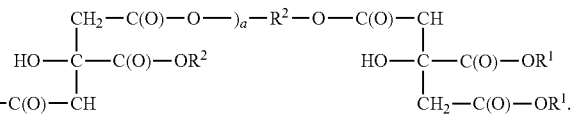

$R^1$ is

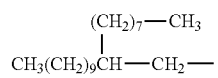

$R^2$ is $-(CH_2CH_2O)_x-CH_2CH_2-$
x is an integer ranging from 8 to 75;
a is an integer ranging from 0 to 20.

Another aspect of the present invention is a process for conditioning hair and skin which comprises contacting the hair or skin with an effective conditioning concentration of a polyester that conforms to the following structure:

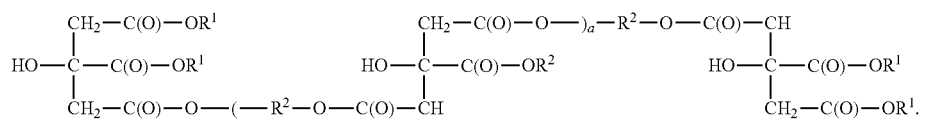

$R^1$ is a mixture of between 15 and 60%

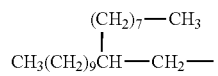

a is an integer ranging from 0 to 20.

In a preferred embodiment said effective conditioning concentration ranges from 0.1% to 20% by weight.

The products of the present invention are made by the esterification reaction of:
(a) citric acid conforming to the following structure:

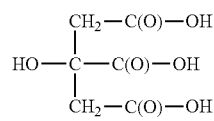

(b) a water soluble diol conforming to the following structure:

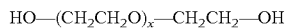

x is an integer ranging from 8 to 75;
(c) octyldodecanol conforming to the following structure:

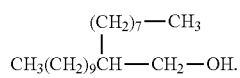

Another aspect of the present invention is a process for conditioning hair and skin which comprises contacting the hair or skin with an effective conditioning concentration of a polyester made by the esterification reaction of:
(a) citric acid conforming to the following structure:

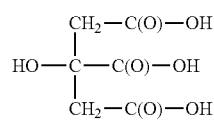

(b) a water soluble diol conforming to the following structure:

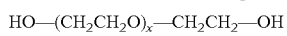

x is an integer ranging from 8 to 75;
(c) octyldodecanol conforming to the following structure:

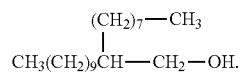

Preferred Embodiments

In a preferred embodiment a is an integer ranging from 1 to 20.

In a preferred embodiment a is an integer ranging from 3 to 10.

In a preferred embodiment a is 10.
In a preferred embodiment a is 15.

EXAMPLES

Example 1

Citric Acid

Citrate is an item of commerce commercially available from a variety of sources including Pfizer. It conforms to the following structure:

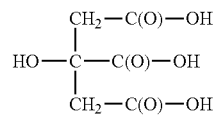

Examples 2-5

Water Soluble Diols

The water soluble diols useful in the present invention are items of commerce sold by many suppliers and conforming to the following structure:

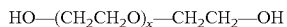

x is an integer ranging from 8 to 75.

Example x
2 8
3 10
4 50
5 75

In the present invention this material provides a linking group that is (a) water soluble, (b) based upon polyoxyethylene and polyoxypropylene compounds, and (c) are easily reacted into the polymer matrix.

Example 6

Octyldodecanol

Octyldodecanol is a Guerbet alcohol commercially available from a variety of sources including Cognis.

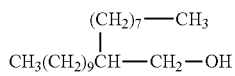

General Procedure

To a suitable reactor equipped with heating and an ability to distill off water is added the specified number of grams of citrate acid (Example 1), finally is added the specified number of grams of the octyldodecanol (Examples 6). The reaction

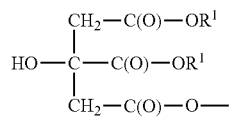

mass is heated to 150-160° C. and water is distilled off. As the reaction proceeds, the batch clears and free citric acid is reacted out. The reaction mass is kept at this temperature until the acid value becomes vanishingly low. Next is added the specified number of grams of the specified water soluble diol (Examples 2-5). The reaction mass is heated to 180-190° C. and water is distilled off. The reaction mass is kept at this temperature until the acid value becomes vanishingly low. The reaction mass is cooled and used without additional purification.

|  | Citric Acid Example 1 | Diol Example 2-5 |  | Guerbet Example 6 |  |
|---|---|---|---|---|---|
| Example | Grams | Example | Grams | Grams | a value |
| 10 | 111 | 2 | 101.5 | 867 | 1 |
| 11 | 120 | 3 | 203.8 | 844 | 2 |
| 12 | 134 | 4 | 1487.7 | 809 | 5 |
| 13 | 144 | 5 | 2769.0 | 785 | 10 |
| 14 | 148 | 2 | 354.2 | 775 | 15 |
| 15 | 150 | 3 | 453.6 | 769 | 20 |

Ex means example in the table above.

Products that are of the present invention were low order liquids that range from very dry easily spread (a is 1-10), to medium viscosity (a is 12-15), to viscous liquids with a lot an outstanding skin feel when applied from aqueous solution or emulsion.

| Example | Water Solubility | Viscosity | Foam | Skin Feel |
|---|---|---|---|---|
| 10 | Dispersible | Low | Low | Fair |
| 13 | Soluble | High | High | Excellent |
| 14 | Soluble | Middle | Middle | Good |
| 15 | Soluble | High | Fair | Excellent |

| Example | Water Solubility | Viscosity | Foam | Skin Feel |
|---|---|---|---|---|

Solubility - 1% Solution in water.
Foam - 1% Solution in water 75 ml shaken in a 250 ml graduated cylinder.
Skin Feel - After drying on skin 1% solution.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A polyester of the following structure

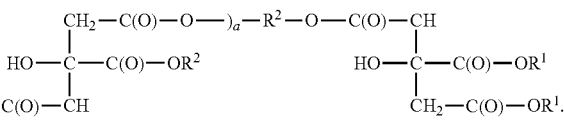

wherein $R^1$ is

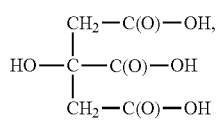

$R^2$ is $-(CH_2CH_2O)_x-CH_2CH_2-$, x is an integer ranging from 8 to 75, and a is an integer ranging from 0 to 20; wherein the polyester is made by an esterification reaction of:

(a) citric acid of the following structure $$\begin{array}{c} CH_2-C(O)-OH, \\ | \\ HO-C-C(O)-OH \\ | \\ CH_2-C(O)-OH \end{array}$$

(b) a water soluble diol of the following structure HO—$(CH_2CH_2O)_x$—$CH_2CH_2$—OH wherein x is an integer ranging form 8 to 75, and (c) octyldodecanol of the following structure

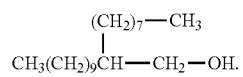

2. A process for conditioning hair and skin which comprises contacting the hair or skin with an effective conditioning concentration of a polyester of the following structure

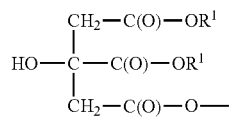 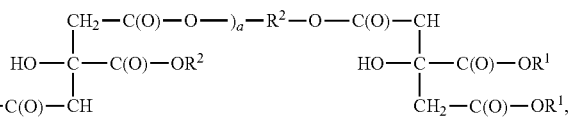

wherein $R^1$ is

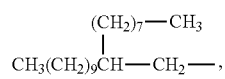

$R^2$ is $-(CH_2CH_2O)_x-CH_2CH_2-$, x is an integer ranging from 8 to 75, and a is an integer ranging from 0 to 20; wherein the polyester is made by an esterification reaction of:

(a) citric acid of the following structure

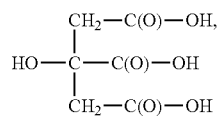

(b) a water soluble diol of the following structure HO—$(CH_2CH_2O)_x$—$CH_2CH_2$—OH wherein x is an integer ranging form 8 to 75, and (c) octyldodecanol of the following structure

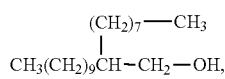

* * * * *